(12) United States Patent
Hoitink et al.

(10) Patent No.: US 10,524,857 B2
(45) Date of Patent: Jan. 7, 2020

(54) DUAL NODE MULTIRAY ELECTRODE CATHETER

(71) Applicant: Biosense Webster (Israel) Ltd., Yokneam (IL)

(72) Inventors: Ryan Hoitink, Pasadena, CA (US); John Hardy Ashton, Glendora, CA (US); Jeffrey L. Clark, Castaic, CA (US); Mario A. Solis, Rancho Cucamonga, CA (US); Shubhayu Basu, Anaheim, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 329 days.

(21) Appl. No.: 14/964,298

(22) Filed: Dec. 9, 2015

(65) Prior Publication Data

US 2017/0071659 A1    Mar. 16, 2017

Related U.S. Application Data

(63) Continuation-in-part of application No. 14/853,653, filed on Sep. 14, 2015, now Pat. No. 10,357,173.

(51) Int. Cl.
*A61B 18/14*    (2006.01)
*A61B 5/042*    (2006.01)
(Continued)

(52) U.S. Cl.
CPC ........ *A61B 18/1492* (2013.01); *A61B 5/0422* (2013.01); *A61B 5/6858* (2013.01);
(Continued)

(58) Field of Classification Search
CPC ................................................. A61B 18/1492
See application file for complete search history.

(56) References Cited

U.S. PATENT DOCUMENTS 5,239,724 A    8/1993    Salecker et al.
5,332,089 A    7/1994    Tillett et al.
(Continued)

FOREIGN PATENT DOCUMENTS

EP    2752153 A1    7/2014
EP    2842604 A1    4/2015
WO    96/05768    2/1996

OTHER PUBLICATIONS

European Search Report from corresponding European Patent Application No. 16202848.4, dated May 8, 2017, pp. 1-8.
(Continued)

*Primary Examiner* — Lee S Cohen
(74) *Attorney, Agent, or Firm* — Dergosits & Noah LLP; Todd A. Noah

(57) ABSTRACT

This disclosure is directed to a catheter having a dual node multiray electrode assembly at the distal end of the catheter body. The dual node multiray electrode assembly includes a proximal multiray array with a plurality of spines connected at one end, each spine having at least one ablation electrode, and a distal node. The dual node multiray electrode assembly may have an expanded configuration and a collapsed configuration wherein the spines are arranged generally along a longitudinal axis of the catheter body. The distal node may be configured to be deployed within a vessel and the proximal multiray array may be configured to engage tissue forming an ostium of the vessel with the ablation electrodes. In some embodiments, the relative distance between the proximal multiray array and the distal node is adjustable.

11 Claims, 5 Drawing Sheets

(51) Int. Cl.
*A61B 5/00* (2006.01)
*A61B 17/00* (2006.01)
*A61B 18/00* (2006.01)
*A61F 2/92* (2013.01)

(52) U.S. Cl.
CPC .. *A61B 5/6859* (2013.01); *A61B 2017/00053* (2013.01); *A61B 2017/00867* (2013.01); *A61B 2018/00267* (2013.01); *A61B 2018/00375* (2013.01); *A61B 2018/00577* (2013.01); *A61B 2018/00839* (2013.01); *A61B 2018/1417* (2013.01); *A61B 2018/1467* (2013.01); *A61F 2/92* (2013.01)

(56) References Cited

U.S. PATENT DOCUMENTS

| | | | |
|---|---|---|---|
| 5,391,199 A | 2/1995 | Ben-Haim | |
| 5,484,118 A | 1/1996 | Fujimura et al. | |
| 5,618,612 A | 4/1997 | Gstrein | |
| 5,672,174 A | 9/1997 | Gough et al. | |
| 5,690,963 A | 11/1997 | Spargo et al. | |
| 5,772,590 A | 6/1998 | Webster, Jr. | |
| 5,855,576 A | 1/1999 | LeVeen | |
| 5,855,592 A | 1/1999 | McGee | |
| 6,064,905 A | 5/2000 | Webster et al. | |
| 6,239,724 B1 | 5/2001 | Doron | |
| 6,315,778 B1 * | 11/2001 | Gambale | A61B 18/1492 606/41 |
| 6,332,089 B1 | 12/2001 | Acker | |
| 6,484,118 B1 | 11/2002 | Govari | |
| 6,618,612 B1 | 9/2003 | Acker | |
| 6,652,517 B1 * | 11/2003 | Hall | A61B 18/1492 606/41 |
| 6,669,693 B2 * | 12/2003 | Friedman | A61B 18/1492 606/41 |
| 6,690,963 B2 | 2/2004 | Ben-Haim | |
| 6,748,255 B2 | 6/2004 | Fuimaono et al. | |
| 6,771,996 B2 * | 8/2004 | Bowe | A61B 18/1492 600/374 |
| 6,973,340 B2 | 12/2005 | Fuimaono et al. | |
| 6,979,331 B2 * | 12/2005 | Hintringer | A61B 18/1492 606/41 |
| 7,344,533 B2 | 3/2008 | Pearson | |
| 7,377,906 B2 | 5/2008 | Selkee | |
| 7,850,685 B2 * | 12/2010 | Kunis | A61B 18/1492 606/41 |
| 8,137,308 B2 | 3/2012 | Schultz | |
| 8,348,940 B2 * | 1/2013 | Behl | A61B 18/1477 606/41 |
| 8,366,705 B2 * | 2/2013 | Arnold | A61B 18/24 606/10 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2005/0080409 A1 | 4/2005 | Young et al. | |
| 2007/0021746 A1 * | 1/2007 | Taimisto | A61B 18/1492 606/41 |
| 2010/0168737 A1 * | 7/2010 | Grunewald | A61B 18/1492 606/41 |
| 2012/0271302 A1 | 10/2012 | Behl et al. | |
| 2013/0103027 A1 | 4/2013 | Sklar et al. | |
| 2013/0237984 A1 | 9/2013 | Sklar | |
| 2014/0194716 A1 * | 7/2014 | Diep | A61B 5/6859 600/374 |
| 2015/0057519 A1 | 2/2015 | Ben-David et al. | |
| 2015/0141987 A1 | 5/2015 | Caplan et al. | |

OTHER PUBLICATIONS

European Search Report from corresponding European Patent Application No. 16202870.8, dated May 10, 2017, pp. 1-8.
European Search Report from corresponding European Patent Application No. 16202871.6, dated May 10, 2017, pp. 1-8.
European Search Report in corresponding European Patent Application No. EP 16188492.9, dated Feb. 9, 2017, pp. 1-8.
Office Action for U.S. Appl. No. 14/853,653; dated Oct. 5, 2017.
Office Action for U.S. Appl. No. 14/853,653; dated Feb. 14, 2018.
Office Action for U.S. Appl. No. 14/964,300; dated Jan. 25, 2018.
Office Action for U.S. Appl. No. 14/964,301; dated Jan. 25, 2018.
U.S. Appl. No. 13/860,921.
U.S. Appl. No. 14/063,477.

* cited by examiner

1

DUAL NODE MULTIRAY ELECTRODE CATHETER

CROSS-REFERENCE TO RELATED APPLICATIONS

This application is a continuation-in-part of commonly-assigned U.S. patent application Ser. No. 14/853,653, filed Sep. 14, 2015, now U.S. Pat. No. 10,357,173, the entire disclosure of which is incorporated by reference.

FIELD OF THE PRESENT DISCLOSURE

This invention relates to electrophysiologic (EP) catheters, in particular, EP catheters for mapping and/or ablation in the heart.

BACKGROUND

Electrophysiology catheters are commonly-used for mapping electrical activity in the heart and/or for delivering ablative energy. Various electrode designs are known for different purposes. For example, catheters having basket-shaped electrode arrays are known and described, for example, in U.S. Pat. Nos. 5,772,590, 6,748,255 and 6,973,340, the entire disclosures of each of which are incorporated herein by reference.

Cardiac arrhythmia, such as atrial fibrillation, occurs when regions of cardiac tissue abnormally conduct electric signals to adjacent tissue, thereby disrupting the normal cardiac cycle and causing asynchronous rhythm Important sources of undesired signals are located in the tissue region along the pulmonary veins of the left atrium. In this condition, after unwanted signals are generated in the pulmonary veins or conducted through the pulmonary veins from other sources, they are conducted into the left atrium where they can initiate or continue arrhythmia.

Procedures for treating arrhythmia include surgically disrupting the origin of the signals causing the arrhythmia, as well as disrupting the conducting pathway for such signals. More recently, it has been found that by mapping the electrical properties of the endocardium and the heart volume, and selectively ablating cardiac tissue by application of energy, it is sometimes possible to cease or modify the propagation of unwanted electrical signals from one portion of the heart to another. The ablation process destroys the unwanted electrical pathways by formation of non-conducting lesions. An example of such an ablation procedure is termed pulmonary vein isolation, and involves the ablation of tissue in the area adjacent the junction of the pulmonary veins and the left atrium. The resulting lesion(s) may isolate irregular electrical signals originating in the area from spreading through the rest of the atrium and disrupting the patient's heart beat.

For these and other applications, conventional practice may involve positioning an ablation catheter adjacent target regions to deliver sufficient energy to form the non-conducting lesions in a circumferential path around a vessel such as a pulmonary vein. Accordingly, it would be desirable to provide a catheter and a technique for facilitating electrical isolation of a source of unwanted signals within such a vessel. Likewise, it would be desirable it reduce or avoid the need to reposition a catheter while performing the ablation procedure. As will be described in the following materials, this disclosure satisfies these and other needs.

SUMMARY

The present disclosure is directed to a catheter with an elongated catheter body having proximal and distal ends and a dual node multiray electrode assembly at the distal end of the catheter body, wherein the dual node multiray electrode assembly comprises a proximal node including a multiray array with a plurality of spines connected at one end, each spine having at least one ablation electrode, and a distal node including a stent, and wherein the dual node multiray electrode assembly has an expanded configuration and a collapsed configuration wherein the spines of the proximal multiray array are arranged generally along a longitudinal axis of the catheter body and the distal node conforms to the catheter body in the collapsed configuration.

In one aspect, the distal node may be configured to be deployed within a vessel in the expanded configuration and wherein the proximal multiray array may be configured to engage tissue of an ostium of the vessel with at least one of the ablation electrodes in the expanded configuration.

In one aspect, the elongated catheter body may have an inner tubular member slidably disposed within a lumen of an outer tubular member and wherein the proximal multiray array may be secured to a distal end of the outer tubular member and the distal node is secured may be a distal end of the inner tubular member. Relative longitudinal movement of the inner tubular member and the outer tubular member may adjust a distance between the proximal multiray array and the distal node.

In one aspect, each spine of the proximal multiray array may have a plurality of independently controlled ablation electrodes.

In one aspect, the spines of the proximal multiray array may curve radially outward in the expanded configuration. The spines may curve proximally or distally.

This disclosure also includes a method for treatment. In one aspect, the method may involve providing a catheter with an elongated catheter body having proximal and distal ends and a dual node multiray electrode assembly at the distal end of the catheter body, wherein the dual node multiray electrode assembly comprises a proximal node including a multiray array with a plurality of spines connected at one end, each spine having at least one ablation electrode, and a distal node including a stent, and wherein the dual node multiray electrode assembly has an expanded configuration and a collapsed configuration wherein the spines of the proximal multiray array are arranged generally along a longitudinal axis of the catheter body and the distal node conforms to the catheter body in the collapsed configuration, positioning the distal end of the catheter at a desired region of the heart, deploying the stent within a vessel in the expanded configuration to engage an inner diameter of the vessel, and positioning the proximal multiray array to bring at least one ablation electrode into contact with tissue forming an ostium of the vessel.

In one aspect, radio frequency energy may be delivered to the ablation electrodes to form lesions. The lesions may be formed in a circumferential path around the ostium of the vessel.

In one aspect, a relative distance between the proximal multiray array and the distal node may be adjusted. Adjusting the relative distance between the proximal multiray array and the distal node may include anchoring the distal node within the vessel and advancing the proximal multiray array towards the distal node to bring the at least one ablation electrode into contact with tissue of the ostium.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

Figure 1:
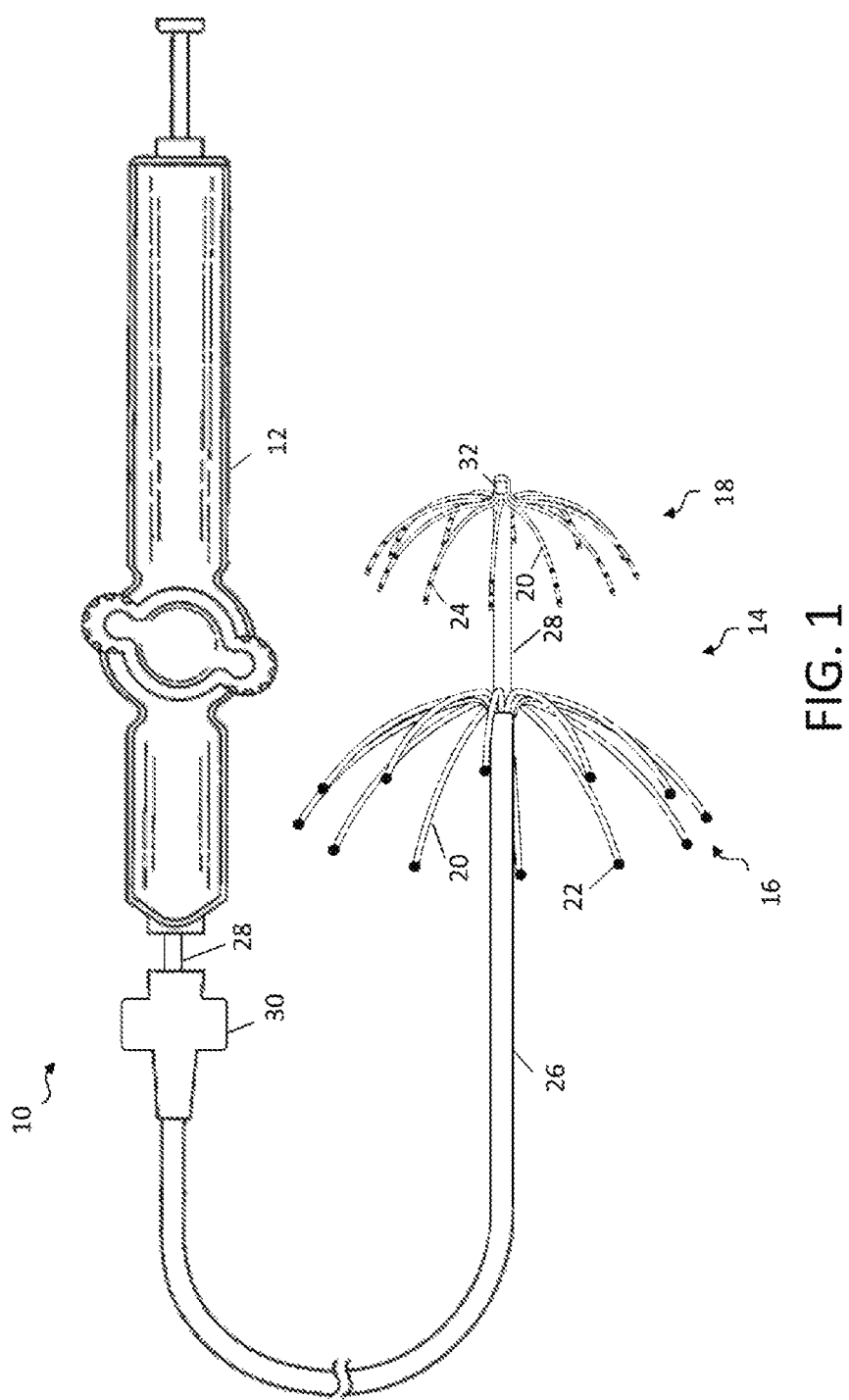
FIG. 1 is a top plan view of a catheter of the present invention, with a dual node multiray electrode assembly in an expanded configuration having spine that curve proximally, according to one embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Certain types of electrical activity within a heart chamber are not cyclical. Examples include atrial fibrillation and other asynchronous conditions that may result from undesired signals originating in the pulmonary veins. As noted, RF energy may be delivered to selected treatment areas with a goal of isolating the source of irregular electrical signals by blocking electrical conduction Important clinical therapies for pulmonary vein isolation include RF ablation via focal or multielectrode catheters.

Focal ablations using unipolar devices benefit from targeted delivery of RF energy along with localized feedback of catheter placement, both spatially and with respect to tissue engagement. However, focal ablation procedures typically involve relative long procedure times as a result of the physician needing to stich a series of "quantized" RF ablation into a continuous circumferential block which surrounds the ostium of the targeted vein. Additionally, the use of a focal unipolar electrode requires substantial physician skill levels augmented with peripheral navigation systems in order to accurately and reliably position the electrode sequentially along the desired circumferential path.

Correspondingly, the use of a multielectrode device seeks to capitalize on the somewhat predictable anatomical structure of the pulmonary vein in order to place an array of unipolar electrodes in a fixed circumferential path around the inner diameter of a targeted vein. RF energy may then be delivered simultaneously to the electrode array, thereby theoretically reducing the time for therapeutic delivery by creating the requisite ablations in parallel. In practice, it has been observed that it may also be difficult to properly orient the electrode array with respect to the ostium of a pulmonary vein and to maintain sufficient engagement between the ablation electrodes and the tissue. Suboptimal tissue engagement results in ineffective energy delivery at some electrode sites and necessitates additional device placements, or in some cases, lesion closure via unipolar ablations from a focal type device.

As will be described herein, this disclosure is directed to a catheter having a dual node multiray electrode assembly. The electrode assembly features a proximal node with multiple spines having a preshaped expanded configuration that facilitates deployment in a desired orientation with respect to a vessel, such as a pulmonary vein. Each spine may carry one or more ablation electrodes. The preshaped expanded configuration may also help ensure sufficient contact between the ablation electrodes and the target tissue to allow proper lesion formation.

The distal node is configured to be deployed within a vessel, such as a pulmonary vein, during the ablation procedure. The distal node may also have multiple spines with a pre-shaped expanded configuration that engages the inner diameter of the vessel to stabilize and orient the electrode assembly, including the proximal node. In some embodiments, each spine of the distal node may carry one or more diagnostic electrodes spaced along the spine to record signals during the procedure.

The use of diagnostic electrodes on the spines of the distal node is advantageous because after an ablation, these diagnostic electrodes can help the user (physician) determine if an effective lesion was created. The user can see if intracardiac signals arriving to the proximal node electrodes are decoupled from signals on the distal node electrodes. Likewise, the user can see if signals arriving to the distal node electrodes are decoupled from signals on the proximal node electrodes. A user could also pace from the proximal node electrodes and verify that there is no capture on the distal node electrodes, or alternatively, pace from the distal node electrodes and verify there is no capture on the proximal node electrodes. This would help the user confirm that an effective lesion has been created because it blocks signals from both directions. Moreover, due to anatomical variations of the pulmonary veins, multiple electrodes on the spines of the distal node would help ensure that at least one electrode along each spine is in contact with the pulmonary vein. This too improves confirmation that an effective lesion was created by seeing decoupled signals between the proximal and distal node electrodes.

In other embodiments, the distal node may employ a different type of expanding structure, such as a balloon, a stent, a basket-shaped electrode assembly or the like, again so that the expanded configuration engages the inner diameter of the vessel in which it deployed to help stabilize the electrode assembly.

To help illustrate these and other aspects of this disclosure, an embodiment as shown in FIG. 1 features catheter 10, having a proximal end with a control handle 12 and a distal end with a dual node multiray electrode assembly 14. Dual node multiray electrode assembly 14 may include a proximal multiray array 16 and a distal multiray array 18, each having a plurality of spines 20. Each spine 20 of proximal multiray array 16 may have one or more ablation electrodes 22, which may be configured as cup or ring electrodes depending on their position along the spine. Similarly, at least one spine 20 of distal multiray array 18 may have one or more diagnostic electrodes 24, which also may be configured as cup or ring electrodes as warranted. In the depicted embodiment, each spine 20 of distal multiray array 18 may have one or more diagnostic electrodes 24. To enable adjustment in the relative distance between proximal multiray array 16 and distal multiray array 18, proximal multiray array 16 may be secured to the distal end of an outer tubular member 26 that is slidably disposed over inner tubular member 28. Control handle 12 may be secured to inner tubular member 28 and an actuator 30 may be secured to the proximal end of outer tubular member 26, so that by manipulating control handle 12 and actuator 30 to slide longitudinally relative to each other, an electrophysiologist may control the distance between proximal multiray array 16 and distal multiray array 18 at the distal end of catheter 10. In some embodiments, dual node multiray electrode assembly 14 may include one or more single- or multi-coil position sensors, such as sensor 32 located in distal multiray array 18. As described below, such position sensors may be used to help determine the position and/or orientation of dual node multiray electrode assembly 14 within the patient. The relative position of proximal multiray array 16 may be determined from the relationship between actuator 30 and control handle 12 or proximal multiray array 16 may also be equipped with a position sensor or sensors as desired.

Inner tubular member 28 and outer tubular members 26 may constitute the catheter body and each may feature an elongated construction with a single, axial or central lumen, but can optionally have multiple lumens if desired. In particular, outer tubular member 26 may have a central lumen within which inner tubular member is coaxially disposed. Inner tubular member 28 may also feature one or more lumens for any suitable purpose, such as to deliver irrigation fluid, and to route cabling and/or leads associated with electrodes 22 and/or 24, position sensor 32, other sensors or for any other suitable purpose.

The numbers of spines 20 forming proximal multiray array 16 and distal multiray array 18 may be the same or different, and may be in the range of approximately 5 to 12 or any other suitable number. Spines 20 may be evenly or unevenly distributed radially. Further, each spine 20 may include multiple electrodes 22 or 24. For ablation electrodes 22, each electrode per spine may be independently controlled as desired. Depending on the number of electrodes employed, they may be evenly distributed along the spine or may be skewed proximally, centrally or distally to facilitate analysis of the measured electrical signals and/or ablation of tissue.

Inner tubular member 28 and outer tubular members 26 are flexible, i.e., bendable, but substantially non-compressible along their lengths. The tubular members may be of any suitable construction and made of any suitable material. One construction comprises an outer wall made of polyurethane or PEBAX® (polyether block amide). The outer wall comprises an imbedded braided mesh of stainless steel or the like to increase torsional stiffness, so that rotation of a proximal end is translated into a corresponding rotation of the distal end, to facilitate guiding and positioning of dual node multiray electrode assembly 14. The outer diameter of outer tubular member 26 is not critical, but generally should be as small as possible and may be no more than about 10 french depending on the desired application. Likewise the thicknesses of the outer walls of the tubular members is not critical, but may be thin enough so that interior lumens can accommodate a puller wire, lead wires, sensor cables and any other wires, cables or tubes. If desired, the inner surface of one or both outer walls may be lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

In one aspect, spines 20 may include a material, such as a shape memory material as described below, that facilitates assuming an expanded arrangement to bring electrodes 22 of proximal multiray array 16 into contact or closer proximity with tissue forming the ostium of a vessel and to cause distal multiray array 18 to engage the inner diameter of the vessel to stabilize dual node multiray electrode assembly 14. Notably, as shown in FIG. 1, in one embodiment spines 20 of proximal multiray array 16 and distal multiray array 18 may have a preshaped configuration in which they form an arc curving in the proximal direction. As will be appreciated, the resiliency associated with the preshaped configurations may facilitate bringing electrodes 22 and/or 24 into contact with the surrounding tissue.

An exemplary construction of spines 20 may include a flexible wire or other structural support strut with a non-conductive covering on which one or more of the electrodes 22 and/or 24 are mounted. In an embodiment, the flexible wires may be formed from a shape memory material to facilitate the transition between expanded and collapsed arrangements and the non-conductive coverings may each comprise a biocompatible plastic tubing, such as polyurethane or polyimide tubing. For example, nickel-titanium alloys known as nitinol may be used. At body temperature, nitinol wire is flexible and elastic and, like most metals, nitinol wires deform when subjected to minimal force and return to their shape in the absence of that force.

Nitinol belongs to a class of materials called Shaped Memory Alloys (SMA) that have interesting mechanical properties beyond flexibility and elasticity, including shape memory and superelasticity which allow nitinol to have a "memorized shape" that is dependent on its temperature phases. The austenite phase is nitinol's stronger, higher-temperature phase, with a simple cubic crystalline structure. Superelastic behavior occurs in this phase (over a 50°-60° C. temperature spread). Correspondingly, the martensite phase is a relatively weaker, lower-temperature phase with a twinned crystalline structure. When a nitinol material is in the martensite phase, it is relatively easily deformed and will remain deformed. However, when heated above its austenite transition temperature, the nitinol material will return to its pre-deformed shape, producing the "shape memory" effect. The temperature at which nitinol starts to transform to austenite upon heating is referred to as the "As" temperature. The temperature at which nitinol has finished transforming to austenite upon heating is referred to as the "Af" temperature.

Accordingly, the dual node multiray electrode assembly 14 may have a three dimensional shape that can be easily collapsed to be fed into a guiding sheath and then readily returned to its expanded shape memory configuration upon delivery to the desired region of the patient upon removal of the guiding sheath. Alternatively, in some embodiments spines 20 can be designed without the internal flexible wire if a sufficiently rigid nonconductive material is used for the non-conductive covering to permit radial expansion of the dual node multiray electrode assembly 14, so long as the spine has an outer surface that is non-conductive over at least a part of its surface for mounting of electrodes.

Figure 2:
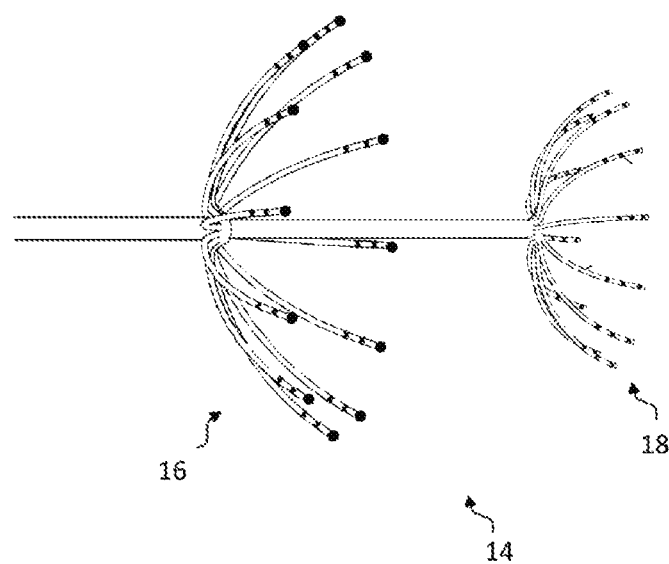
FIG. 2 is a schematic view of a dual node multiray electrode assembly having an expanded configuration with spines that curve distally, according to one embodiment.

Other configurations of spines 20 may be employed, such as shown in FIG. 2 in which the spines curve in the distal direction. In this embodiment, proximal multiray array 16 employs spines 20 that have multiple ablation electrodes 22. Alternatively, the spines 20 of proximal multiray array 16 and distal multiray array 18 may curve in either combination of opposing directions. Regardless of the orientation of their curvature, spines 20 may be sized appropriately depending on the patient's anatomy. For example, spines 20 of proximal multiray array 16 may have a length and/or curvature configured to engage tissue forming the ostium of the vessel, while spines 20 of distal multiray array 18 may have a length and/or curvature adapted to form an expanded configuration that engages the inner diameter of the vessel. In some embodiments, the outer diameter assumed by the expanded configuration of distal multiray array 18 may be relatively smaller than the outer diameter assumed by proximal multiray array 16.

As indicated above, this disclosure also includes embodiments in which dual node multiray electrode assembly 14 employs a proximal multiray array 16 similar to that described above but distal multiray array 18 may be replaced by a different expandable distal node.

Figure 3:
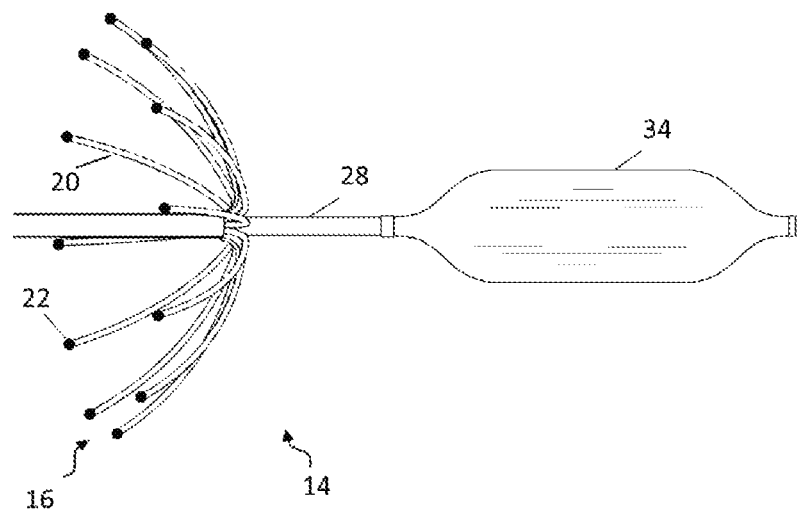
FIG. 3 is a schematic view of a dual node multiray electrode with an inflatable balloon distal node, according to one embodiment.

For example, FIG. 3 schematically illustrates an embodiment in which the distal node is implemented using inflatable balloon 34. Balloon 34 may employ any suitable construction, such as those associated with angioplasty procedures or stent deployment. In its unexpanded, collapsed configuration, balloon 34 may conform closely to the outer diameter of inner tubular member 28. Once positioned at a desired location within a patient's vessel, balloon 34 may be inflated, such as by the use of a suitable inflation fluid, until it assumes an expanded configuration that engages the inner diameter of the vessel to help stabilize dual node multiray electrode assembly 14.

Figure 4:
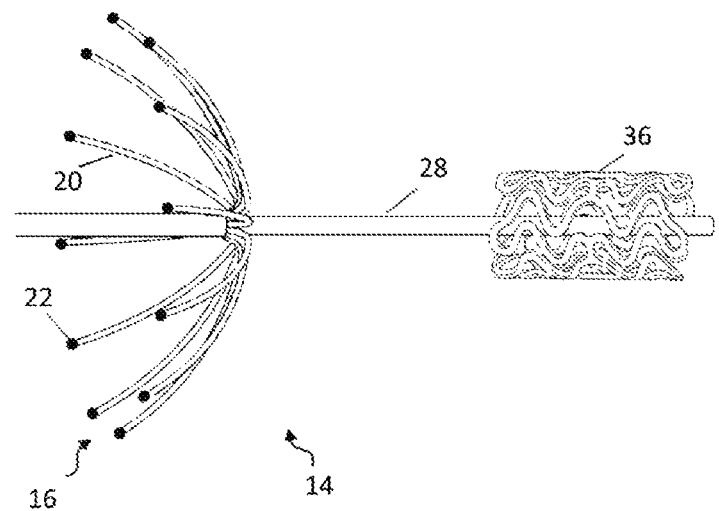
FIG. 4 is a schematic view of a dual node multiray electrode with a stent distal node, according to one embodiment.

In another example, FIG. 4 schematically illustrates an embodiment in which the distal node of dual node multiray electrode assembly 14 is implemented using stent 36, or other similar expandable intraluminal device. Stent 36 may have an unexpanded, collapsed configuration that conforms closely to the outer diameter of inner tubular member 28. Likewise, stent 36 may be expanded using any technique as known to those of skill in the art once positioned at a desired location within a patient's vessel. In its expanded configuration, stent 36 may engage the inner diameter of the vessel thereby stabilizing dual node multiray electrode assembly 14.

Figure 5:
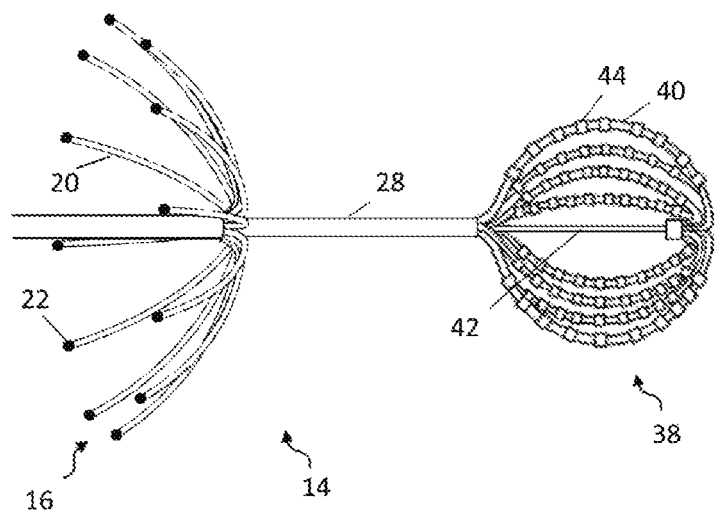
FIG. 5 is a schematic view of a dual node multiray electrode with a basket-shaped electrode assembly distal node, according to one embodiment.

Yet another example is schematically depicted in FIG. 5. In this embodiment, the distal node of dual node multiray electrode assembly 14 is configured as a basket-shaped electrode assembly 38. Basket assembly 38 has a plurality of spines 40 connected at their proximal and distal ends. Basket-shaped electrode assembly 38 has an expanded arrangement wherein spines 40 bow radially outwardly and a collapsed arrangement wherein spines 40 are arranged generally along the axis of the catheter body. In some embodiments, the distance between the proximal and distal ends of basket-shaped electrode assembly 38 may be shortened, such as by moving puller wire 42 proximally, causing spines 40 to bow outwards into the expanded configuration.

Alternatively, the construction of spines 40 may be similar to that of spines 20, for example with respect to the use of shape memory materials that may cause basket-shaped electrode assembly 38 to assume its expanded configuration when unconstrained, such as by being advanced out of inner tubular member 28. As desired, spines 40 may also carry one or more diagnostic electrodes 44 to measure electrical signals from within the vessel when basket-shaped electrode assembly 38 is deployed. When basket-shaped electrode assembly 38 assumes its expanded configuration, spines 40 may engage the inner diameter of the vessel thereby stabilizing dual node multiray electrode assembly 14.

Figure 6:
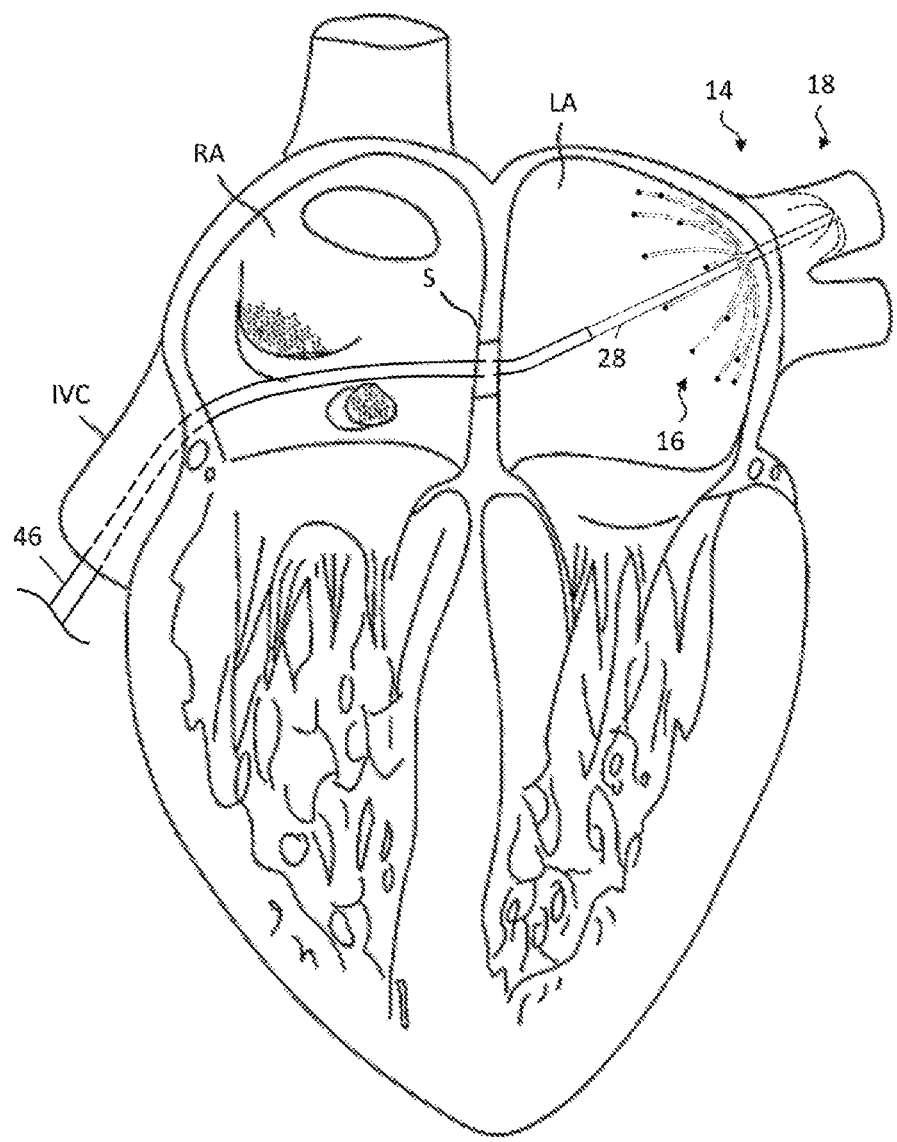
FIG. 6 is a schematic view of a dual node multiray electrode positioned within the left atrium, according to one embodiment.

In one aspect, an electrophysiologist may introduce a guiding sheath, guide wire and dilator into the patient, as is generally known in the art. Examples of suitable guiding sheaths for use in connection with the inventive catheter are the PREFACE™. Braided Guiding Sheath (commercially available from Biosense Webster, Inc., Diamond Bar, Calif.) and the DiRex™. Guiding Sheath (commercially available from BARD, Murray Hill, N.J.). The guide wire is inserted, the dilator is removed, and the catheter is introduced through the guiding sheath whereby the guide wire lumen in the expander permits the catheter to pass over the guide wire. In one exemplary procedure as depicted in FIG. 6, catheter 10, disposed within guiding sheath 46 is first introduced to the right atrium (RA) via the inferior vena cava (IVC), where it passes through the septum (S) in order to reach the left atrium (LA).

As will be appreciated, guiding sheath 46 covers the spines 20 of the dual node multiray electrode assembly 14 in a collapsed position so that the entire catheter can be passed through the patient's vasculature to the desired location. Once the distal end of the catheter reaches the desired location, e.g., the left atrium adjacent a pulmonary vein, guiding sheath is withdrawn to expose the dual node multiray electrode assembly 14. Once the guiding sheath is withdrawn, spines 20 flex outwardly and assume their expanded configuration, such that distal multiray array 18 may engage the inner diameter of the vessel (shown in phantom) and proximal multiray array 16 to bring one or more ablation electrodes 22 into contact with tissue at desired regions.

In one aspect, multiple electrodes 22 may be in contact in a circumferential path around an ostium of a vessel, e.g., a pulmonary vein. In another aspect, embodiments may allow adjustment of relative distance between the proximal node and the distal node, for example by using the techniques discussed above or others. Correspondingly, manipulation of actuator 30 and control handle 12 provides control over the relative position of proximal multiray array 16 and distal multiray array 18 through inner tubular member 28 and outer tubular member 26.

As will be appreciated, a procedure employing a dual node multiray electrode assembly with the techniques of this disclosure allow any desired sequence of operations to be performed, including, but not limited to: expanding or allowing to expand either or both the proximal and the distal node; adjusting relative positioning between the proximal and distal nodes; recording electrical signals; and delivering energy for ablation. As an illustration, one non-limiting aspect may involve deploying the distal node within a vessel to serve as an anchor, adjusting the relative longitudinal position of the proximal node to facilitate bringing one or more electrodes into a desired degree of contact with tissue on a circumferential path around the ostium of the vessel. Correspondingly, RF energy may be delivered to the ablation electrodes to ablate tissue in a circumferential path around the inner vessel wall. Depending upon the number of spines 20 and the number electrodes being employed, a substantially complete circumferential lesion may be formed simultaneously in some embodiments.

In other embodiments, catheter 10 may be rotated after forming a first set of lesions, so that electrodes 20 come into contact with new areas of tissue along the circumferential path and the delivery of ablation energy may then be repeated. The sequence of rotation and delivery of energy may be repeated as warranted. Formation of a substantially complete lesion around the circumference of the vessel may electrically isolate the source of abnormal signals as described above.

Figure 7:
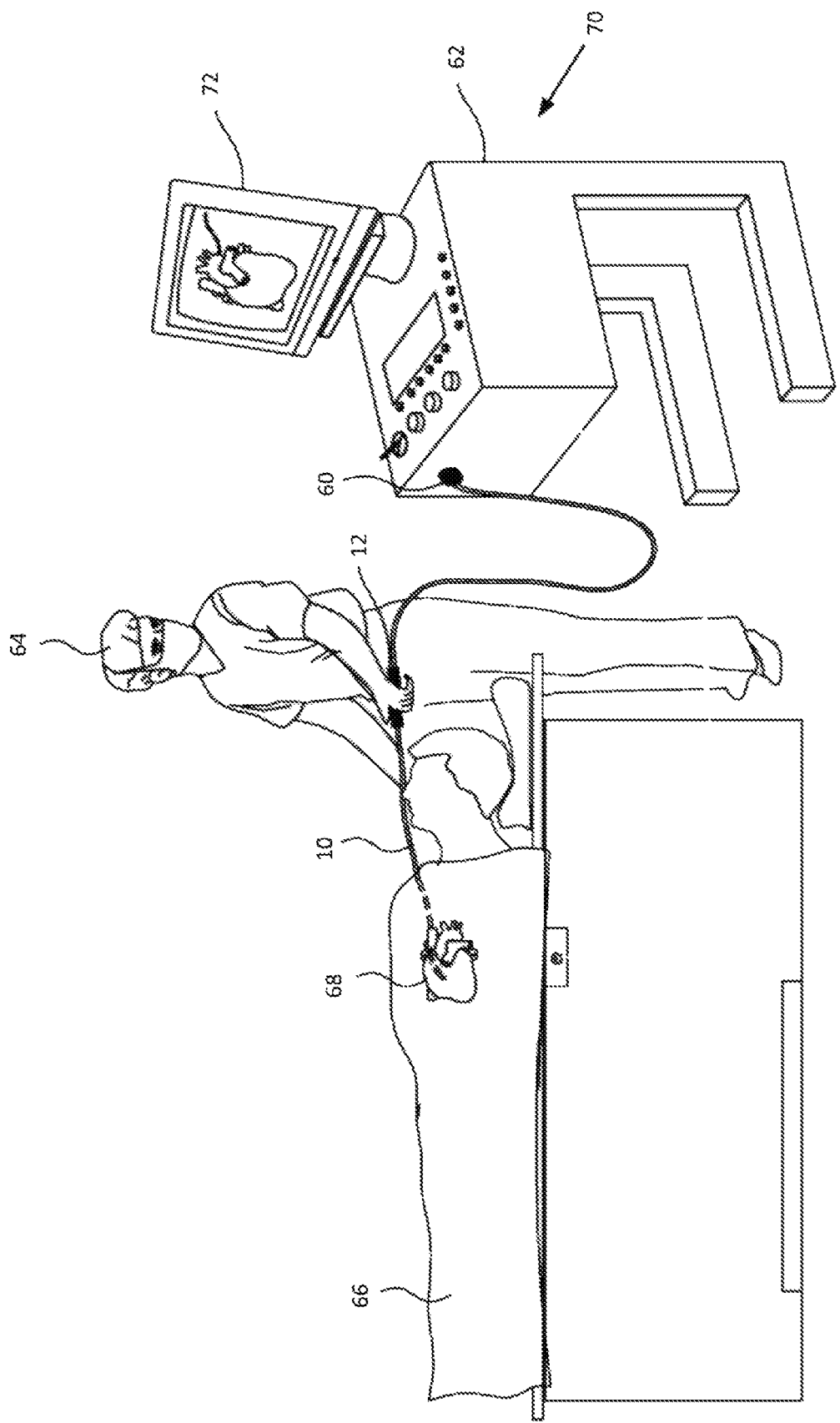
FIG. 7 is a schematic illustration of an invasive medical procedure using a dual node multiray electrode assembly, according to one embodiment.

To help illustrate use of dual node multiray electrode assembly 14, FIG. 7 is a schematic depiction of an invasive medical procedure, according to an embodiment of the present invention. Catheter 10, with the dual node multiray electrode assembly 14 (not shown in this view) at the distal end may have a connector 60 at the proximal end for coupling the leads of the electrodes and sensors (not shown in this view) to a console 62 for recording and analyzing the signals they detect as well as for supplying ablating energy. An electrophysiologist 64 may insert the catheter 10 into a patient 66 in order to acquire electropotential signals from the heart 68 of the patient, such as via electrodes 24 of distal multiray array 18. The electrophysiologist 64 uses the control handle 12 attached to the catheter in order to perform the insertion.

Console 62 may include a processing unit 70 which analyzes the received signals, and which may present results of the analysis on a display 72 attached to the console. The results are typically in the form of a map, numerical displays, and/or graphs derived from the signals. Processing unit 70 may also control the delivery of energy to electrodes 20 of proximal multiray array 16 for creating one or more lesions. The electrophysiologist 64 may perform the operations described above to create a substantially complete circumferential lesion.

Further, the processing unit 70 may also receive signals from position sensors, such as sensor 32 (not shown in this view). As noted, the sensor(s) may each comprise a magnetic-field-responsive coil or a plurality of such coils. Using a plurality of coils enables six-dimensional position and orientation coordinates to be determined The sensors may therefore generate electrical position signals in response to the magnetic fields from external coils, thereby enabling processor 70 to determine the position, (e.g., the location and orientation) of the distal end of catheter 10 within the heart cavity. The electrophysiologist may then view the position of the dual node multiray electrode assembly 14 on an image the patient's heart on the display 72. By way of example, this method of position sensing may be implemented using the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference. As will be appreciated, other location sensing techniques may also be employed. In one aspect, the coordinates of the distal sensor relative to the proximal sensor may be determined and, with other known information pertaining to the configuration of dual node multiray electrode assembly 14, used to find the positions of each of the electrodes 22 and/or 24.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising an elongated catheter body having proximal and distal ends and a dual node multiray electrode assembly at the distal end of the catheter body, wherein the dual node multiray electrode assembly comprises a proximal node including a multiray array with a plurality of spines connected only at one end, each spine having at least one ablation electrode and a distal node including a stent, and wherein the dual node multiray electrode assembly has an expanded configuration and a collapsed configuration wherein the spines of the proximal multiray array are arranged generally along a longitudinal axis of the catheter body and the distal node conforms to the catheter body in the collapsed configuration, the elongated catheter body comprising an inner tubular member slidably disposed within a lumen of an outer tubular member, a proximal end of the inner tubular member being secured to a control handle, the proximal node multiray array being secured to a distal end of the outer tubular member and the distal node being secured to a distal end of the inner tubular member.

2. The catheter of claim 1, wherein the distal node is configured to be deployed within a vessel in the expanded configuration and wherein the proximal multiray array is configured to engage tissue of an ostium of the vessel with the at least one ablation electrode in the expanded configuration.

3. The catheter of claim 1, wherein relative longitudinal movement of the inner tubular member and the outer tubular member adjusts a distance between the proximal multiray array and the distal node.

4. The catheter of claim 1, wherein each spine of the proximal multiray array comprises a plurality of independently controlled ablation electrodes.

5. The catheter of claim 1, wherein the spines of the proximal multiray array curve radially outward in the expanded configuration.

6. The catheter of claim 5, wherein the spines of the proximal multiray array curve proximally.

7. The catheter of claim 5, wherein the spines of the proximal multiray array curve distally.

8. A method for treatment comprising:
providing a catheter with an elongated catheter body having proximal and distal ends and a dual node multiray electrode assembly at the distal end of the catheter body, wherein the dual node multiray electrode assembly comprises a proximal node including a multiray array with a plurality of spines connected only at one end, each spine having at least one ablation electrode and a distal node including a stent, and wherein the dual node multiray electrode assembly has an expanded configuration and a collapsed configuration wherein the spines of the proximal multiray array are arranged generally along a longitudinal axis of the catheter body and the distal node conforms to the catheter body in the collapsed configuration, the elongated catheter body comprising an inner tubular member slidably disposed within a lumen of an outer tubular member, a proximal end of the inner tubular member being secured to a control handle, the proximal node multiray array being secured to a distal end of the outer tubular member and the distal node being secured to a distal end of the inner tubular member;

positioning the distal end of the catheter at a desired region of the heart;

deploying the stent within a vessel in the expanded configuration to engage an inner diameter of the vessel; and positioning the proximal multiray array to bring at least one ablation electrode into contact with tissue forming an ostium of the vessel.

9. The method of claim 8, further comprising delivering radio frequency energy to the at least one ablation electrode to form a substantially complete circumferential lesion.

10. The method of claim 8, further comprising adjusting a relative distance between the proximal multiray array and the distal node.

11. The method of claim 10, wherein adjusting the relative distance between the proximal multiray array and the distal node comprises anchoring the distal node within the vessel and advancing the proximal multiray array towards the distal node to bring the at least one ablation electrode into contact with tissue of the ostium.

* * * * *